(12) United States Patent
Ala-Paavola et al.

(10) Patent No.: US 12,031,972 B2
(45) Date of Patent: Jul. 9, 2024

(54) MEASUREMENT DEVICE AND METHOD

(71) Applicant: MATO ENGINEERING OY, Espoo (FI)

(72) Inventors: Jaakko Ala-Paavola, Espoo (FI); Marko Oikarinen, Espoo (FI)

(73) Assignee: MATO ENGINEERING OY, Espoo (FI)

( * ) Notice: Subject to any disclaimer, the term of this patent is extended or adjusted under 35 U.S.C. 154(b) by 375 days.

(21) Appl. No.: 17/437,866

(22) PCT Filed: Mar. 12, 2020

(86) PCT No.: PCT/FI2020/050156
§ 371 (c)(1),
(2) Date: Sep. 10, 2021

(87) PCT Pub. No.: WO2020/183065
PCT Pub. Date: Sep. 17, 2020

(65) Prior Publication Data
US 2022/0170903 A1    Jun. 2, 2022

(30) Foreign Application Priority Data

Mar. 12, 2019  (FI) ............................. 20195179
Mar. 12, 2019  (FI) ............................. 20195180

(51) Int. Cl.
*G01N 33/38* (2006.01)
*G01N 7/14* (2006.01)
(52) U.S. Cl.
CPC ............. *G01N 33/383* (2013.01); *G01N 7/14* (2013.01)

(58) Field of Classification Search
CPC .......... G01N 33/383; G01N 7/10; G01N 7/14; G01N 15/08; G01N 7/00; G01N 15/0826;
(Continued)

(56) References Cited

U.S. PATENT DOCUMENTS

2004/0004554 A1   1/2004  Srinivasan et al.
2004/0153270 A1   8/2004  Yamashita et al.
(Continued)

FOREIGN PATENT DOCUMENTS

CA       2093196 C       12/2003
CN     101603937 A       12/2009
(Continued)

OTHER PUBLICATIONS

Finnish Search Report issued by the Finnish Patent and Registration Office in relation to Finnish Application No. 20195179 dated Sep. 25, 2019 (1 page).
(Continued)

*Primary Examiner* — John Fitzgerald
*Assistant Examiner* — Truong D Phan
(74) *Attorney, Agent, or Firm* — Robert P. Michal, Esq.; Carter, DeLuca & Farrell LLP

(57) ABSTRACT

A measurement device and method for measuring concrete curing. The measurement device includes a closed air-filled chamber, chamber walls defining a closed air-filled chamber space inside the closed air-filled chamber, and a pressure sensor provided inside the air-filed chamber space of the closed air-filled chamber. The chamber walls are arranged air and water vapour permeable allowing air and water vapour flow into the closed air-filled chamber space and out of closed air-filled chamber space.

16 Claims, 11 Drawing Sheets

(58) Field of Classification Search
CPC . G01N 33/38; G01N 2291/0232; G01N 15/00
See application file for complete search history.

(56) References Cited

U.S. PATENT DOCUMENTS

| | | |
|---|---|---|
| 2009/0100926 A1 | 4/2009 | Kanare et al. |
| 2009/0206853 A1 | 8/2009 | Hawkins |
| 2010/0128751 A1 | 5/2010 | Doll |
| 2014/0216143 A1 | 8/2014 | Salmi et al. |
| 2015/0135846 A1 | 5/2015 | Pagani et al. |
| 2017/0212094 A1 | 7/2017 | Radjy |
| 2017/0364039 A1 | 12/2017 | Schober et al. |
| 2018/0011076 A1 | 1/2018 | Radjy et al. |
| 2018/0052146 A1 | 2/2018 | Radjy |
| 2018/0340925 A1 | 11/2018 | Radjy et al. |
| 2018/0371754 A1 | 12/2018 | Harrison et al. |

FOREIGN PATENT DOCUMENTS

| | | | |
|---|---|---|---|
| CN | 102495112 B | 6/2013 | |
| CN | 102680168 B | 11/2013 | |
| CN | 204758030 U | 11/2015 | |
| CN | 109814177 A | 5/2019 | |
| DE | 102012208050 A1 | 11/2013 | |
| EP | 0027718 A1 * | 4/1981 | |
| EP | 1942344 A1 | 7/2008 | |
| EP | 2746765 A1 | 6/2014 | |
| EP | 2510212 B1 | 11/2014 | |
| EP | 2699901 B1 | 8/2017 | |
| EP | 3236258 A2 | 10/2017 | |
| GB | 1179906 A | 2/1970 | |
| GB | 2569159 A | 6/2019 | |
| JP | S5879147 A | 5/1983 | |
| JP | 2005078473 A | 3/2005 | |
| KR | 20130085775 A | 7/2013 | |
| NO | 172664 B | 5/1993 | |
| WO | 0223158 A1 | 3/2002 | |
| WO | 2013030430 A1 | 3/2013 | |
| WO | WO-2013170973 A1 * | 11/2013 | ........... G01N 33/383 |
| WO | 2016051026 A1 | 4/2016 | |

OTHER PUBLICATIONS

Finnish Search Report issued by the Finnish Patent and Registration Office in relation to Finnish Application No. 20195180 dated Sep. 12, 2019 (2 pages).

Chang, C-Y and S-S Hung Implementing RFIC and sensor technology to measure temperature and humidity inside concrete structures. In: Construction and Building Materials Netherlands: Elsevier, Jun. 18, 2011, vol. 26, 628-637, ISSN 0950-0618, <DOI:10.1016/j.conbuildmat.2011.06.066>, XP028285575 see the entire document, especially abstract; section 2.2. "Design and experiment of encapsulation box"; figure 5.

International Search Report issued by the Finnish Patent and Registration Office acting as the International Searching Authority in relation to International Application No. PCT/FI2020/050160 dated Jun. 12, 2020 (5 pages).

International Search Report issued by the Finnish Patent and Registration Office acting as the International Searching Authority in relation to International Application No. PCT/FI2020/050159 dated Jun. 30, 2020 (6 pages).

International Search Report issued by the Finnish Patent and Registration Office acting as the International Searching Authority in relation to International Application No. PCT/FI2020/050156 dated Jun. 12, 2020 (8 pages).

Written Opinion of the Interntional Searching Authority issued by the Finnish Patent and Registration Office acting as the International Searching Authority in relation to International Application No. PCT/FI2020/050156 dated Jun. 12, 2020 (12 pages).

* cited by examiner

MEASUREMENT DEVICE AND METHOD

CROSS-REFERENCE TO RELATED APPLICATIONS

This application is a national phase entry under 35 U.S.C. 371 of PCT International Application No. PCT/FI2020/050156 filed Mar. 12, 2020, which claims priority to Finnish Patent Application No. 20195179, filed Mar. 12, 2019 and Finnish Patent Application No. 20195180, filed Mar. 12, 2019, the disclosure of each of these applications is expressly incorporated herein by reference in their entirety.

FIELD OF THE INVENTION

The present invention relates to a measure device for measuring concrete curing. The present invention also relates to a method for measuring concrete curing.

BACKGROUND OF THE INVENTION

Curing of concrete is a process by which a freshly casted concrete is protected against loss of moisture required for hydration. Curing of concrete will increase the strength and decrease the permeability of hardened concrete. Curing also prevents formation of thermal and plastic cracks, which can severely impact durability of structures. Curing process involves keeping the concrete moist until the hydration of concrete is complete and required strength is achieved. Curing of concrete should be started soon after initial setting time of casted concrete and should be continued for a reasonable period of time for the concrete to achieve its desired strength and durability.

In the curing process, it is important to maintain an uninterrupted hydration after concrete is casted. Uniform temperature should also be maintained throughout the concrete to avoid thermal shrinkage cracks. Accordingly, curing concrete is a process designed primarily to retain the concrete moist till the end of hydration.

In the prior art, concrete curing process is controlled by measuring moisture and temperature of the concrete during the curing process. However, the problem of controlling the curing process is that the prior art moisture and temperature measurements have usually a delay to actual moisture content and temperature of the cured concrete. Accordingly, when the moisture measurement indicate that the moisture of the concrete is at low level during the curing process, the moisture content of concrete easily drops too low as absorption of water into the concrete takes time during and after wetting the concrete with water. This causes incomplete curing and deterioration of strength of the concrete. Further, this may cause cracks to the concrete.

BRIEF DESCRIPTION OF THE INVENTION

An object of the present invention is to provide measurement device for measuring concrete curing. The measurement device comprises a closed air-filled chamber, chamber walls defining a closed air-filled chamber space inside the closed air-filled chamber, and a pressure sensor provided inside the air-filed chamber space of the closed air-filled chamber. The chamber walls are provided air and water vapour permeable allowing air and water vapour flow into the closed air-filled chamber space and out of closed air-filled chamber space.

Accordingly, the pressure sensor is provided inside a closed air-filled chamber provided with a flow path allowing air and water vapour flow into and out of the closed air-filled chamber space. This, enables the pressure sensor to measure pressure variations inside the air-filled chamber space. Further, during concrete curing water evaporation causes loss of water from the concrete and further the curing of concrete consumes water. This loss of water generates capillary pressure inside the concrete. The capillary pressure inside the concrete generates under pressure or decrease of pressure due to the loss or deficiency of water inside the concrete. Similarly, excess of water inside the concrete may cause over pressure or increase in pressure inside the concrete.

When the pressure sensor is provided inside air-filled chamber according to the present invention, the pressure may be measured inside the closed air-filled chamber as the capillary under pressure or decrease of pressure inside the concrete causes flow of air and water vapour out of the closed air-filled chamber through the air and water vapour permeable flow path. In this situation, the air inside closed air-filled chamber space may expand and/or flow out of the closed air-filled chamber space via the air and water vapour permeable chamber walls. Thus, decrease in pressure inside the closed air-filled chamber space is generated.

Similarly, increase in pressure or moisture inside concrete causes air and water vapour to flow into the closed air-filled chamber space through the air and water vapour permeable flow path. Thus, excess or increased moisture in the concrete air and water vapour to flow into the closed air-filled chamber space through the air and water vapour permeable flow path compressing the air inside the closed air-filled chamber space such that pressure inside the closed air-filled chamber space is generated.

In one embodiment of the present invention, the chamber walls are made of air and water vapour permeable material and arranged to define the closed air-filled chamber space inside the closed air-filled chamber.

This, provides a closed air-filled chamber having air and water vapour permeable walls enabling air and water vapour flow in and out of the closed air-filled chamber space.

In one embodiment, the closed air-filled chamber comprises inner chamber walls defining the closed air-filled chamber space inside the closed air-filled chamber, outer chamber walls arranged to surround the first chamber walls outside the closed air-filled chamber space, and a closed chamber air gap provided between the inner chamber walls and the outer chamber walls such that the outer chamber walls are provided at a distance from the inner chamber walls.

The closed chamber air gap provides a capillary break between the closed air-filled chamber and outside the closed air-filled chamber. The capillary break prevents capillary water flow into the closed air-filled chamber space.

In one embodiment, the inner chamber walls and the outer chamber walls are made of air and water vapour permeable material allowing air and water vapour flow into the closed air-filled chamber space and out of closed air-filled chamber space through the inner chamber walls and the outer chamber walls. This allows efficient air and water vapour flow into and out of the closed air-filled chamber space.

In another embodiment, the inner chamber walls are made of air and water vapour permeable material and the outer chamber walls are provided air and water vapour impermeable and comprise an outer wall flow channel provided with an air and water vapour permeable outer wall barrier element for providing flow path for air and water vapour into the closed air-filled chamber space and out of closed air-filled chamber space through the inner chamber walls and outer wall barrier element.

In a further embodiment, the inner chamber walls are provided air and water vapour impermeable and comprise an inner wall flow channel provided with an air and water vapour permeable inner wall barrier element and the outer chamber walls are provided air and water vapour impermeable and comprise an outer wall flow channel provided with an air and water vapour permeable outer wall barrier element for providing flow path for air and water vapour flow into the closed air-filled chamber space and out of closed air-filled chamber space through the inner wall barrier element and outer wall barrier element.

In a yet other embodiment, the inner chamber walls are provided air and water vapour impermeable and comprise an inner wall flow channel provided with an air and water vapour permeable inner wall barrier element and the outer chamber walls are made of air and water vapour permeable material for providing flow path for air and water vapour flow into the closed air-filled chamber space and out of closed air-filled chamber space through the inner wall barrier element and the outer chamber walls.

In one embodiment, the air and water vapour permeable material of the inner chamber walls and the outer chamber walls is porous material for providing air and water vapour permeability. The porous material enables air and water vapour flow efficiently into and out of the closed air-filled chamber space.

The porous material enables air and water vapour flow through the material. Air and water vapour may flow through the material via the pores of the porous material.

In one embodiment, the air and water vapour permeable material of the inner chamber walls and the outer chamber walls comprises one of the following: mineral-based material, or concrete, or cement-based material, or calcium sulfate dehydrate-based material.

In the context of this application mineral -based material means inorganic and non-metallic material. Examples of mineral -based material are glass materials or the like.

In one embodiment, the inner wall barrier element and the outer wall barrier element are made of porous material for providing air and water vapour permeability. Accordingly, the air and water vapour may flow through the first and second barrier elements and via the chamber air gap into and out of the closed air-filled chamber and chamber space.

The porous material of the inner wall barrier element and the outer wall barrier element comprises one of the following mineral-based material, or, concrete, or cement-based material, calcium sulfate dehydrate -based material.

Cements and concrete based material may be preferable when measuring concrete curing as they behave similarly as the measured concrete.

Calcium sulfate dehydrate may be preferable as it has a neutralizing property, thereby reducing the effect of acidic or alkaline vapors, and additionally binds any salts present in the water vapor inside the closed air-filled chamber space.

Pore-size of the porous material of the inner wall barrier element and the outer wall barrier element is between, 1 to 100 nm, or 3 to 30 nm, or 5 to 20 nm.

The pore-size have an effect on the water vapour flow in the porous material or in the barrier element. Too small pore-size, under 1 nm, prevents water vapour from flowing or the flow is slow. On the other hand, too large pore-sized over 1 or several micrometers may cause liquid water entering the closed air-filled chamber space.

In one embodiment, the chamber walls are provided air and water vapour impermeable. Thus, the chamber walls prevent air and water vapour from flowing into the closed air-filled chamber space.

In one embodiment, the chamber walls comprise a flow channel between the closed the closed air-filled chamber space inside the closed air-filled chamber and the outside of the closed air filled chamber. The flow channel comprises a first barrier element arranged define the closed air-filled chamber space together with the chamber walls. The first barrier element is air and water vapour permeable. The first barrier element blocks or closes the flow channel such that air and water vapour flow into and out of the closed air-filled chamber space occurs through the first barrier element.

In one embodiment, the flow channel comprises a second barrier element arranged to the flow channel outside closed air-filled chamber space and at distance from the first barrier element such that a closed first air gap is provided between the first and second barrier elements. The second barrier element is air and water vapour permeable for providing flow path for air and water vapour flow into the closed air-filled chamber space and out of closed air-filled chamber space through flow channel and the first and second barrier elements and via the closed first air gap.

The closed first air gap is provided to the flow channel between the first and second barrier elements.

In one embodiment, first barrier element or the second barrier element or the first and second barrier elements are made of porous material for providing air and water vapour permeability. Thus, the porous material provides air and water vapour flow through flow channel and the first and second barrier elements and via the closed first air gap.

In some embodiments, the porous material of the first and second barrier elements comprises one of the following: mineral-based material, or concrete, or cement-based material, or calcium sulfate dehydrate -based material.

The effect of these different materials is disclosed above.

The material of the first and second barrier elements may be same or different. Similarly, the material of the inner chamber wall and the outer chamber wall maybe same or different.

In some embodiments, pore-size of the porous material of the first and second barrier elements is between 1 to 100 nm, or 3 to 30 nm, or 5 to 20 nm.

The effect of different pore-sizes is disclosed above.

Pore-size of the porous material of the first and second barrier elements may be same or different. Similarly, pore-size of the porous material of the inner chamber wall and the outer chamber wall maybe same or different.

In one embodiment, the measurement device comprises a housing surrounding the closed air-filled chamber. The housing being air and water vapour permeable. The housing encloses the closed air-filed chamber and allows air and water vapour flow into the closed air-filled chamber space via the flow channel.

In one embodiment, the measurement device comprises a housing surrounding the closed air-filled chamber. The housing 40 comprising a housing barrier element. The housing barrier element is air and water vapour permeable and arranged to provide flow path for air and water vapour between the closed air-filled chamber and outside of the housing.

The housing encloses the closed air-filed chamber and housing barrier element allows air and water vapour flow into the closed air-filled chamber space via the flow channel.

In one embodiment, the air and water vapour permeable housing or the air or water vapour permeable housing barrier element is arranged to form the first barrier element or the second barrier element. Thus, the separate second barrier element may be omitted. The first closed first air gap is provided between the first barrier element and the housing or the housing barrier element.

In one embodiment, the measurement device comprises a housing surrounding the closed air-filled chamber. The housing comprising one or more openings arranged to provide flow path for air and water vapour between the closed air-filled chamber and outside of the housing.

Accordingly, air and water vapour may flow into the flow channel and/or into the closed air-filled chamber space via the one or more openings in the housing.

In one embodiment, the closed air-filled chamber space further comprises a temperature sensor.

In another embodiment, the closed air-filled chamber space further comprises a humidity sensor.

In a further embodiment, the closed air-filled chamber space further comprises a temperature sensor and a humidity sensor.

The present invention further provides a method for measuring concrete curing with a measurement device. The method comprises arranging the measurement device into freshly casted concrete. The method comprises measuring concrete curing with a measurement device as disclosed above. The method further comprises allowing air and water vapour to flow into and out of the closed air-filled chamber space of the measurement device, and measuring pressure inside the closed air-filled chamber space with the pressure sensor provided inside the air-filed chamber space of the measurement device.

Accordingly, the concrete curing may be measured by measuring pressure variations. The pressure variations are caused by water deficiency or excess in the curing concrete. The loss of water cannot be instantly measured with humidity or moisture measurements, as the concrete usually is moist during curing even if there is deficiency of water for effective curing the strength development. However, humidity and moisture measurement are effective for measuring drying of the concrete.

In one embodiment, the method comprises measuring humidity with a humidity sensor provided inside the air-filed chamber space of the measurement device.

In another embodiment, method comprises measuring temperature with a temperature sensor provided inside the air-filed chamber space of the measurement device.

Humidity measurements and temperature measurements are effective for measuring concrete drying.

In one embodiment, the method comprises measuring the pressure inside the closed air-filled chamber space with the pressure sensor provided inside the air-filled chamber space of the measurement device, and detecting decrease in measured pressure value and providing indication of the detected decrease in measured pressure value.

Alternatively, the method comprises detecting increase in measured pressure value, and providing indication of the detected increase in measured pressure value.

Further alternatively, the method comprises detecting decrease or increase in measured pressure value, and providing indication of the detected decrease or increase in measured pressure value.

The present invention further relates to use of the measurement device for measuring concrete curing by pressure measurement with the pressure sensor provided inside the air-filed chamber space of the measurement device.

The present invention also comprises use of the measurement device for measuring concrete drying by pressure measurement with the pressure sensor and humidity sensor provided inside the air-filed chamber space of the measurement device.

The present invention also comprises use of the measurement device for measuring wetness of material surface by pressure measurement with the pressure sensor provided inside the air-filled chamber space of the measurement device. The measurement device is arranged on the surface of the material.

The present invention yet further comprises use of the measurement device for measuring wetness of a road surface by pressure measurement with the pressure sensor provided inside the air-filled chamber space of the measurement device. The measurement device is arranged on the surface of the road.

According to the above mentioned, the measurement device may be concrete curing measurement device.

Alternatively, the measurement device may be a humidity or moisture measurement device.

Further alternatively, the measurement device may be a material surface wetness or road surface wetness measurement device. Further, the measurement device may be a road surface condition measurement device arranged to measure both wetness and temperature on the road surface.

When measuring the wetness of material surface or road surface, the measurement device may be arranged on the surface of the material or road on at partly inside the material or road such that the measurement device forms part of the material surface or road surface. Alternatively, the measurement device may be arranged fully inside or embedded into the material or road, if the material or road is provided with flow openings to the measurement device or is made of air and water vapour permeable material.

The air and water vapour permeable housing, housing barrier elements and the inner and outer chamber walls and the first and second barrier elements, allow air and water vapour flow into and out of the closed air-file chamber space when the outer surface of the measurement device is on contact with water or moisture. This allows, the measurement of wetness of material or road surface.

According to the present invention, the porous material or the barrier elements may absorb water or water vapour. Thus, the pressure variations inside the closed air-filled chamber space are caused by amount of water or water vapour in the porous material or the barrier elements in relation to the water or water vapour concentration or amount outside the measurement device or the porous material or the barrier elements. When water or water vapour flows out of the porous material or the barrier elements outside the measurement device due to loss or deficiency of water in the surroundings of the measurement device, decrease in pressure in the closed air-filled chamber occurs. Similarly, when water or water vapour flows into the porous material or the barrier elements from outside the measurement device due to excess or increased amount water in the surroundings of the measurement device, increase in pressure in the closed air-filled chamber occurs.

The present invention provides a quick and exact information of changings in moisture conditions surrounding the measurement device. The pressure inside the closed air-filled chamber space provides quick response to changing moisture conditions inside the concrete and on a material surface. This provides an efficient method for controlling concrete curing. During concrete curing the concrete consumes water which may be seen as decreased pressure in the closed air-filled chamber space. Thus, the loss of water may be detected and the curing concrete may be wetted accordingly at right time such that strength development of the concrete may be provided optimal and advantageous as cracking of concrete may be avoided.

BRIEF DESCRIPTION OF THE DRAWINGS

The invention is described in detail by means of specific embodiments with reference to the enclosed drawings, in which.

DETAILED DESCRIPTION OF THE INVENTION

Figure 1:
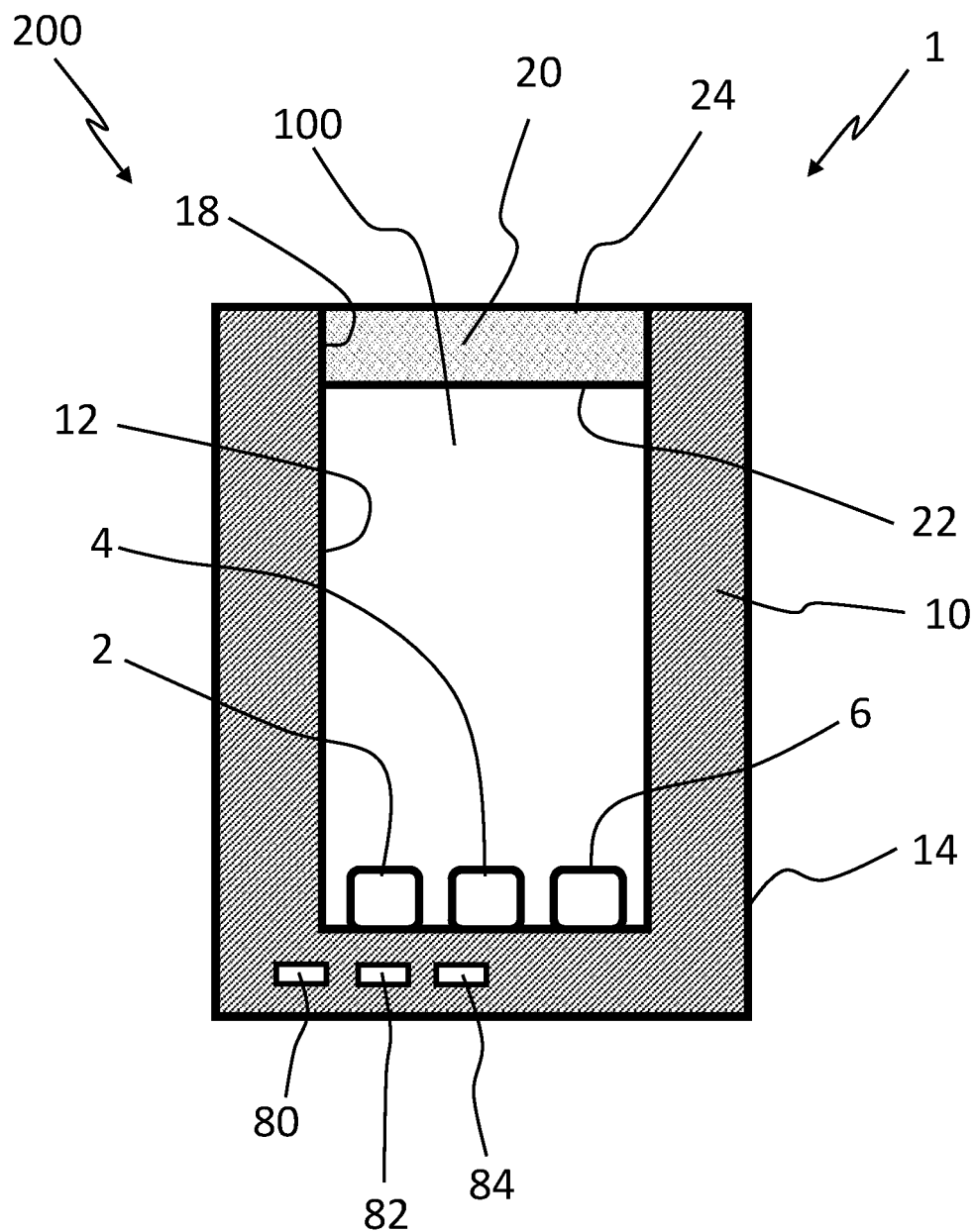
FIGS. 1 and 2 show schematically one embodiment of a measurement device according to the present invention.

FIG. 1 shows one embodiment of the measurement device 1 according to the present invention. The measurement device 1 comprises a closed air-filled chamber 200. The measurement device 1 comprises chamber walls 10 defining a closed air-filled chamber space 100 inside the closed air-filled chamber 200. The chamber walls 10 are provided air and water vapour impermeable such that air and water vapour may not flow through the chamber walls 10.

The chamber walls 10 have an outer chamber wall surface 14 and an inner chamber wall surface 12. The inner surface defines the closed air-filled chamber space 100.

The chamber walls 10 comprise a flow channel 18 between the closed the closed air-filled chamber space 100 inside the closed air-filled chamber 200 and the outside of the closed air filled chamber 200, as shown in FIG. 1. The flow channel 18 is provided with a first barrier element 20 arranged to the flow channel 18. The first barrier element 20 blocks or closes the flow channel 18. The first barrier element 20 is arranged to define the closed air-filled chamber space 100 together with the chamber walls 10.

The first barrier element 20 comprises a first barrier inner surface 22 defining the closed air-filled chamber space 100 together with inner chamber wall surface 12 of the chamber walls 10.

The first barrier element 20 comprises a first barrier outer surface 24 defining outer surface of the closed air-filled chamber 200 together with outer chamber wall surface 14 of the chamber walls 10.

The first barrier element 20 is air and water vapour permeable enabling air and water vapour flow into and out of the closed air-filled chamber space 100 through the flow channel 18.

The measurement device 1 further comprises a pressure sensor 2 provided inside the air-filed chamber space 100 of the closed air-filled chamber 200.

The pressure sensor 2 may be any know pressure sensor, or any known pressure sensor capable of measuring air temperature.

The measurement device 1 further comprises a temperature sensor 4 provided inside the closed air-filled chamber space 100 of the closed air-filled chamber 200 for measuring temperature inside the closed air-filled chamber space 100. The temperature sensor 4 may be any know temperature sensor.

The measurement device 1 further comprises a humidity sensor 6 provided inside the closed air-filled chamber space 100 of the closed air-filled chamber 200 for measuring humidity inside the closed air-filled chamber space 100. The humidity sensor 6 may be any know humidity sensor.

It should be noted, that the temperature sensor 4 and/or the humidity sensor 6 may also be omitted.

As shown in FIG. 1, the measurement device 1 further system components for operating the measurement device 1 and the sensors 2, 4, 6. The system components are connected to the sensors 2, 4, 6. The system components may comprise a power source 80, such as battery, a transmitter 82 for transmitting measurement data to external device or server system, and an antenna 84. The system components may also comprise a memory and a processor. The measurement data may be transmitted via Internet of Things to cloud computing. Internet of Thing can be connected by using The Long Range Wide Area Network, as an example. The Long Range Wide Area Network, LoRaWAN, specification is a Low Power, Wide Area networking protocol designed to wirelessly connect battery operated things to the internet in regional, national or global networks. The benefit of LoRaWAN is long battery life. The measurement device 1 may be programmed to go into deep sleep mode when not transmitting messages, which maximizes battery life. Further, the LoRa signal itself requires a small power to generate and transmit. Further, cellular based technologies like NB-IOT and Cat-M can also be used for transmitting the measurement data.

Figure 2:
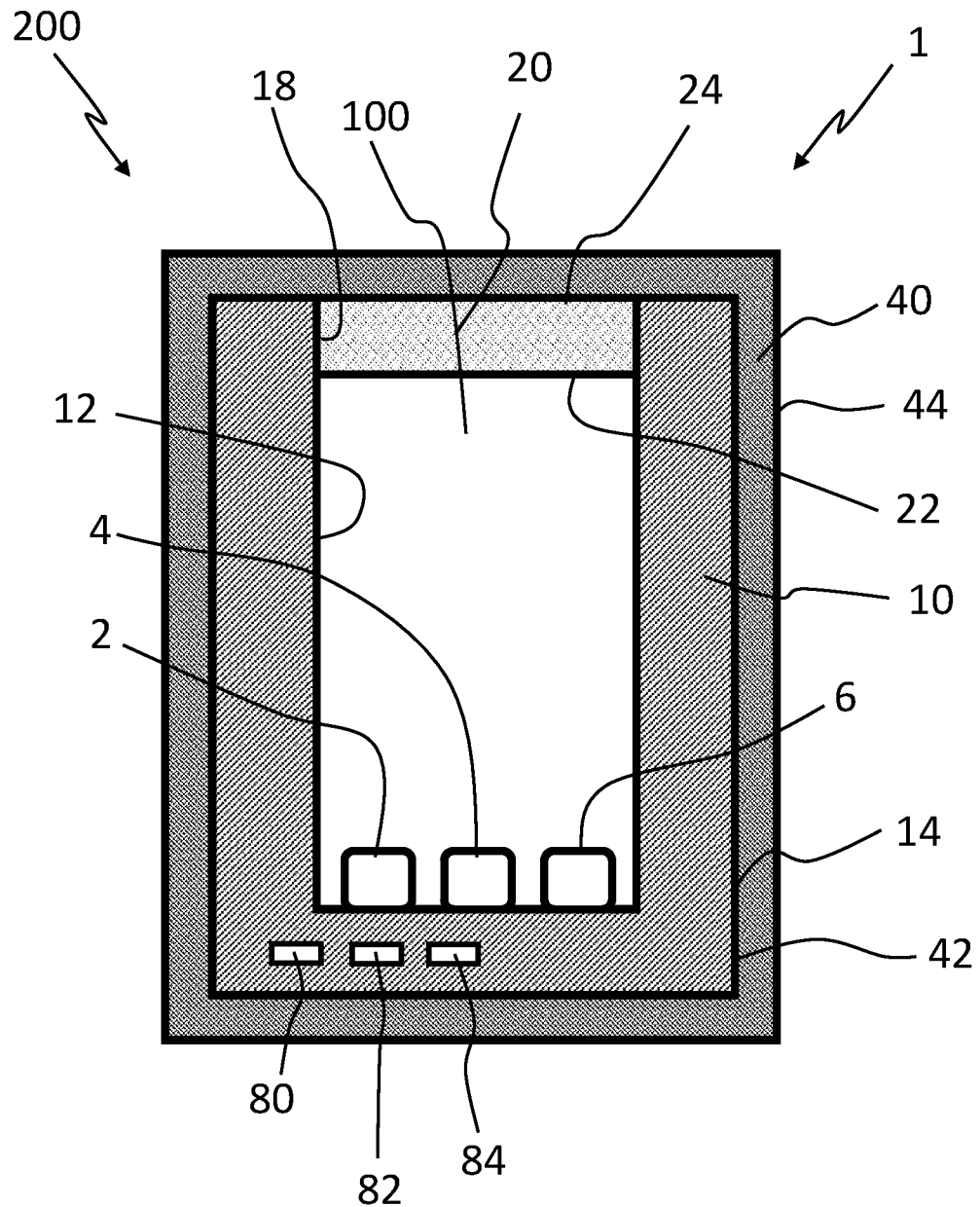

FIG. 2 shows one embodiment, comprising the closed air-filled chamber 200 of FIG. 1. In this embodiment, the measurement device 1 comprises a housing 40 surrounding the closed air-filled chamber 200. The housing 40 encloses the closed air-filled chamber 200. The housing 40 comprises an outer housing surface 44 forming the outer surface of the measurement device 1. The housing 40 also comprises inner housing surface 42 towards the closed air-filled chamber 200.

In this embodiment, the housing 40 is made of air and water vapour permeable material such that air and water vapour may pass through the housing 40 to the flow channel 18 and further into and from the closed air-filled chamber space 100.

Figure 3:
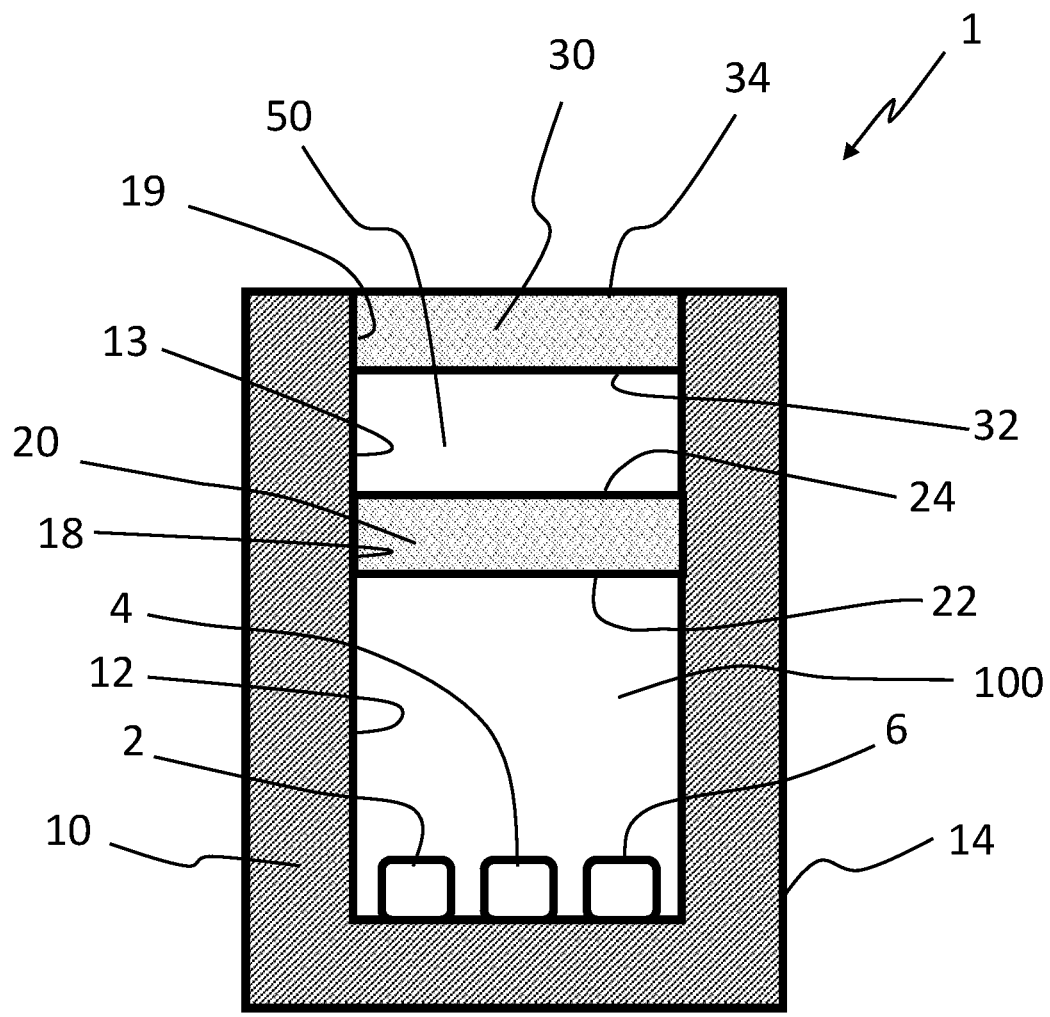
FIGS. 3, 4 and 5 show schematically another embodiment of a measurement device according to the present invention.

FIG. 3 shows an alternative embodiment in which the chamber walls 10 are provided air and water vapour impermeable such that air and water vapour may not flow through the chamber walls 10.

The chamber walls 10 comprise a flow channel 18, 13, 19 between the closed the closed air-filled chamber space 100 inside the closed air-filled chamber 200 and the outside of the closed air filled chamber 200, as shown in FIG. 3. The flow channel 18, 13, 19 is provided with the first barrier element 20 arranged to the flow channel 18, 13, 19. The first barrier element 20 blocks or closes the flow channel 18, 13, 19. The first barrier element 20 is arranged to define the closed air-filled chamber space 100 together with the chamber walls 10.

The first barrier element 20 comprises the first barrier inner surface 22 defining the closed air-filled chamber space 100 together with inner chamber wall surface 12 of the chamber walls 10.

The flow channel 18, 13, 19 further comprises a second barrier element 30 arranged to the flow channel 18, 13, 19 outside closed air-filled chamber space 100 and at distance from the first barrier element 20 such that a closed first air gap 50 is provided between the first and second barrier elements 20, 30. The second barrier element 30 blocks or closes the flow channel 18, 13, 19.

The first barrier element 20 comprises the first barrier outer surface 24. The second barrier element 30 comprises the second barrier inner surface 32 towards the first barrier outer surface 24 of the first barrier element 20.

The second barrier element 30 comprises the second barrier outer surface 32 facing away from the first barrier element 20 of the first barrier element 20.

The first air gap 50 is formed between the first and second barrier elements 20, 30 in the flow channel 18, 13, 19. The first air gap 50 is formed between the first barrier outer surface 24 of the barrier element 20 and the second barrier inner surface 32 of the second barrier element 30 in the flow channel 18, 13, 19.

The first air gap 50 provides a capillary break to the flow channel 18, 13, 19 between the first and second barrier elements 20, 30. Thus, flow on liquid water to the closed air-filled chamber space 100.

The second barrier element is air and water vapour permeable for providing flow path for air and water vapour flow into the closed air-filled chamber space 100 and out of closed air-filled chamber space 100 through flow channel 18, 13, 19 and the first and second barrier elements 20, 30 and via the closed first air gap 50.

Figure 4:
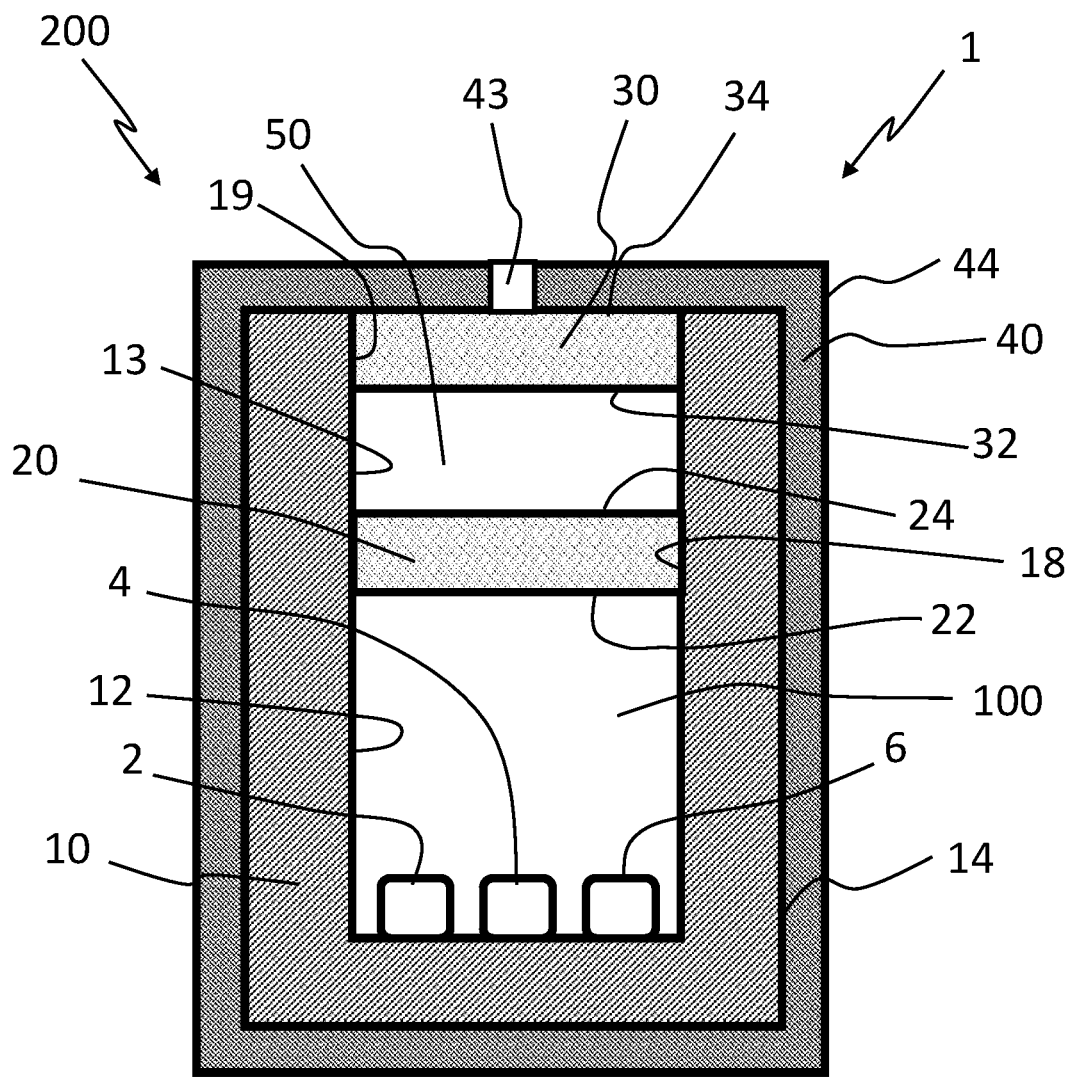

FIG. 4 shows a modification of the measurement device 1 comprising the closed air-filled chamber 200 of FIG. 3. The measurement device 1 comprises a housing 40 surrounding the closed air-filled chamber 200. The housing 40 comprises one or more openings 43 arranged to provide flow path for air and water vapour between the closed air-filled chamber 200 and outside of the housing 40. The housing 40 in this embodiment is made of air and water impermeable material.

Alternatively, the housing 40 of FIG. 4 may also be made of air and water permeable material.

In this embodiment, air and water vapour ay flow through the one or more openings 43 to the flow channel 18, 13, 19 and further into and from the closed air-filled chamber space 100.

Figure 5:
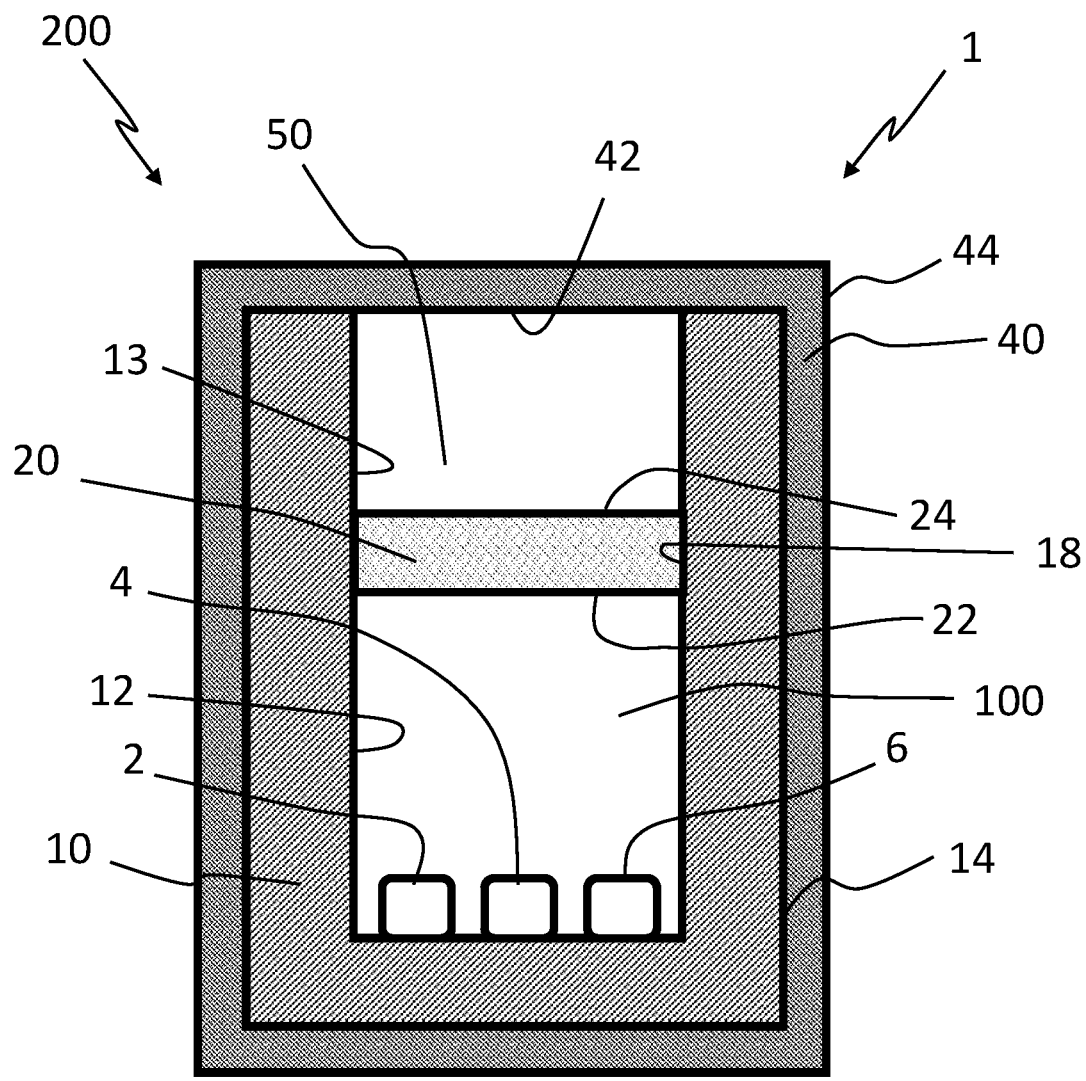

FIG. 5 shows an embodiment which corresponds the closed air filled chamber 200 of FIG. 3. In this embodiment, the second barrier elements 30 is omitted. The housing 40 is made of air and water vapour permeable material and arranged to enclose the closed air-filled chamber 200. The housing 40 is further arranged to close the flow channel 18, 13 of the closed air-filled chamber 200.

The housing 40 or the housing inner wall 42 is arranged at a distance from the first barrier element 20 such that the first air gap 50 is formed between the housing 40 and the first barrier element 20 in the flow channel 18, 13. Furthermore, the first air gap 50 is formed between the inner housing wall 42 and the first barrier outer surface 24 of the first barrier element 20. Accordingly, the first air gap 50 provides the capillary break.

Figure 6:
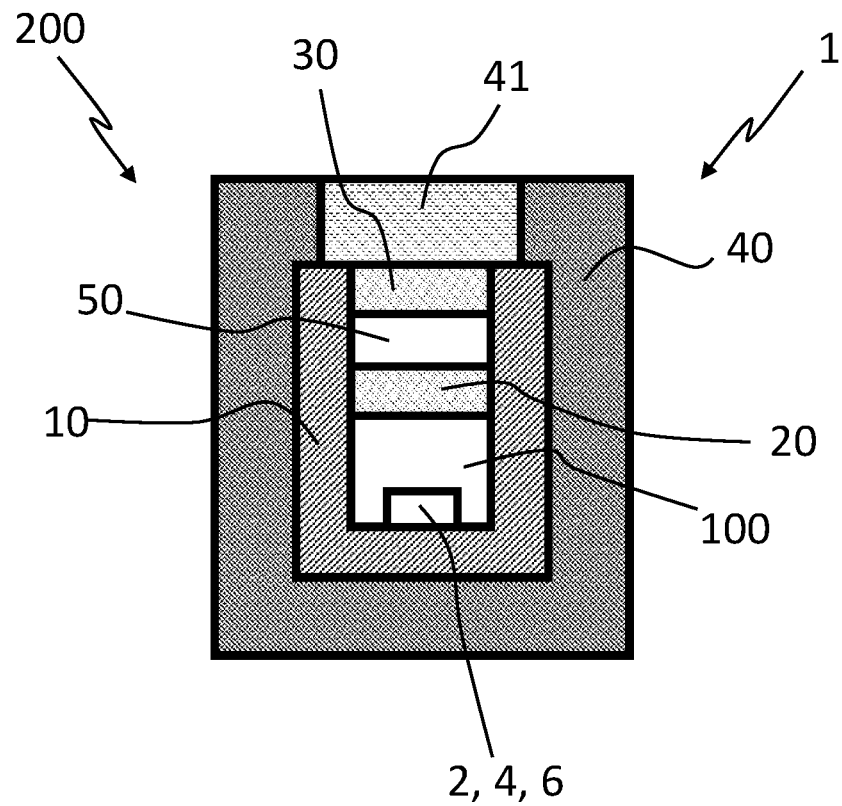
FIGS. 6, 7 and 8 show different embodiments a measurement device of FIGS. 3 with a housing.

FIG. 6 shows an embodiment, in which the measurement device 1 comprises the first and second barrier elements 20, 30 in the flow channel 18, 13, 19. The measurement device 1 further comprises the housing 40 surrounding and enclosing the closed air-filled chamber 200. The housing 40 is made of air and water vapour impermeable material. The housing is further provided with a housing barrier element 41. The housing barrier element 41 is air and water vapour permeable and arranged to provide flow path for air and water vapour between the closed air-filled chamber 200 and outside of the housing 40.

The housing barrier element 41 is arranged in fluid communication with the flow channel 18, 13, 19 and the first and second barrier elements 20, 30 such that air and water vapour may flow between the outside of the housing 40 and the closed air-filled chamber space 100.

Figure 7:
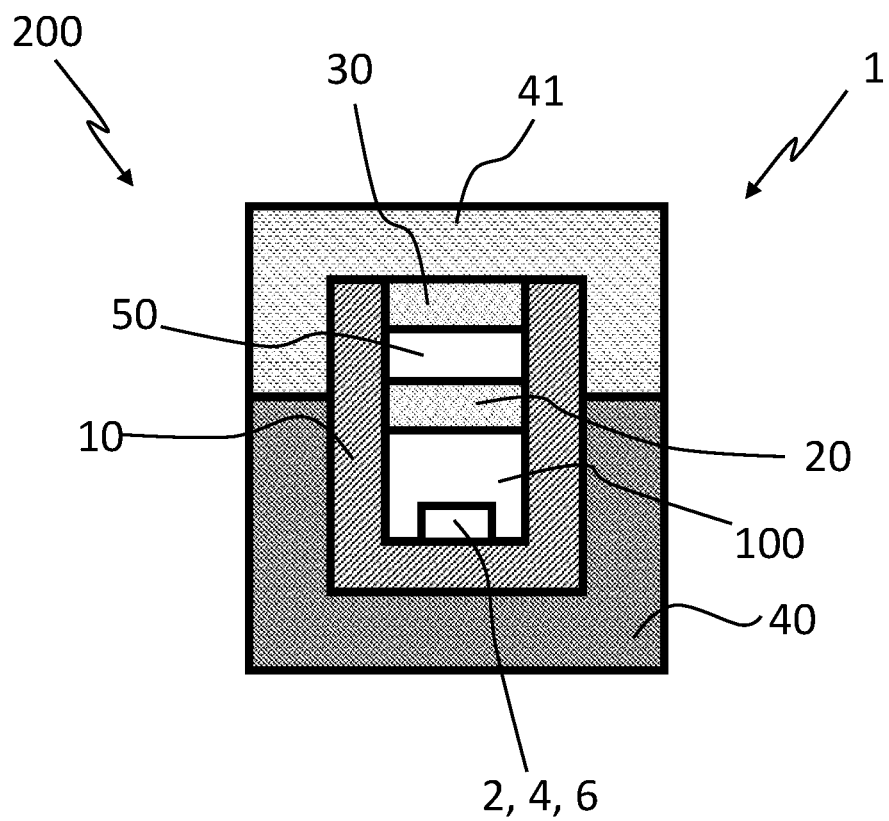

FIG. 7 shows an alternative embodiment in which the measurement device 1 comprises the first and second barrier elements 20, 30 in the flow channel 18, 13, 19. The measurement device 1 further comprises the housing 40, 41 surrounding and enclosing the closed air-filled chamber 200. The housing 40, 41 is formed from a first housing part 40 made of air and water vapour impermeable material and a second housing part made of air and water vapour permeable material. The second housing part 41 is provided in connection with the flow channel 18, 13, 19 of the closed air-filled chamber 200 such that air and water vapour may flow between the outside of the housing 40 and the closed air-filled chamber space 100 through the second housing part 41.

Figure 8:
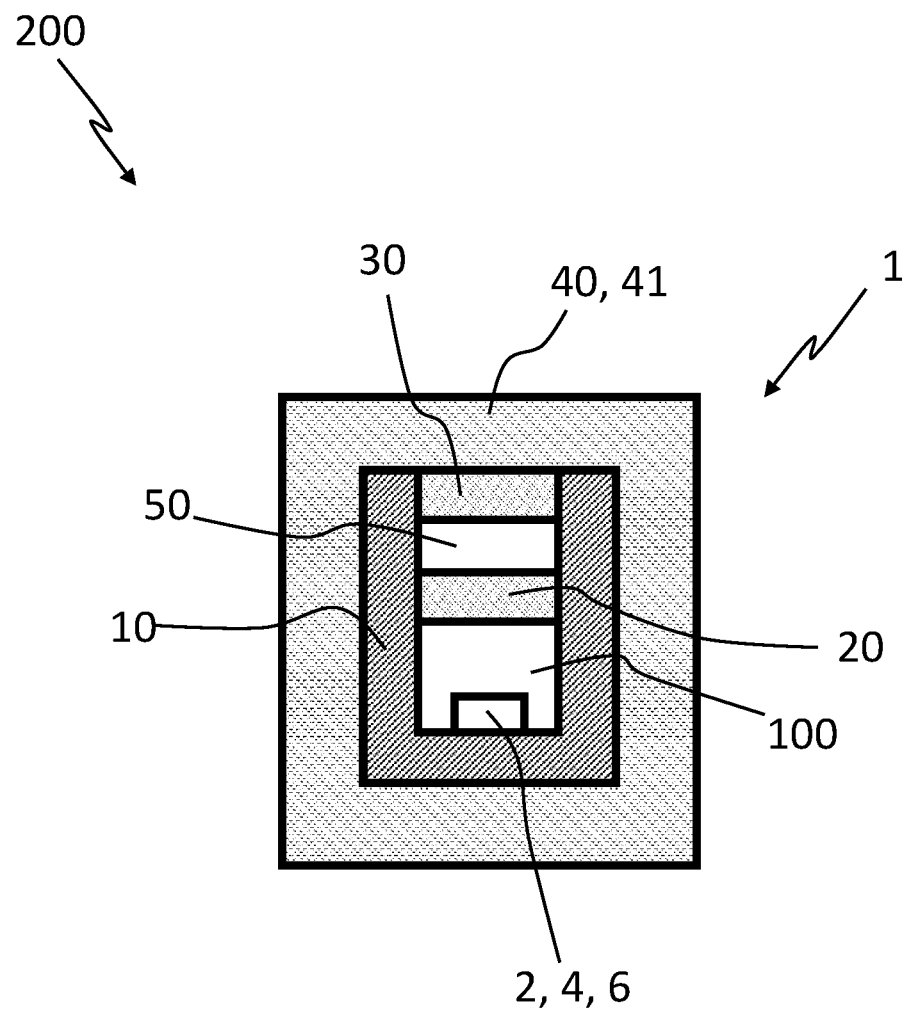

FIG. 8 shows a further embodiment in which the shows an embodiment, in which the measurement device 1 comprises the first and second barrier elements 20, 30 in the flow channel 18, 13, 19. The measurement device 1 further comprises the housing 40 surrounding and enclosing the closed air-filled chamber 200. The housing 40 is made of air and water vapour permeable material. The housing 40 is arranged in fluid communication with the flow channel 18, 13, 19 and the first and second barrier elements 20, 30 such that air and water vapour may flow between the outside of the housing 40 and the closed air-filled chamber space 100.

In the embodiments of FIGS. 6, 7 and 8, the measurement device 1 comprises the first and second barrier elements 20, 30. However, the second barrier element 30 may also be omitted such that the first air gap 50 is formed between the air and water vapour permeable housing 40, second housing part 41 or the housing barrier element 41 and the first barrier element 20.

Figure 9:
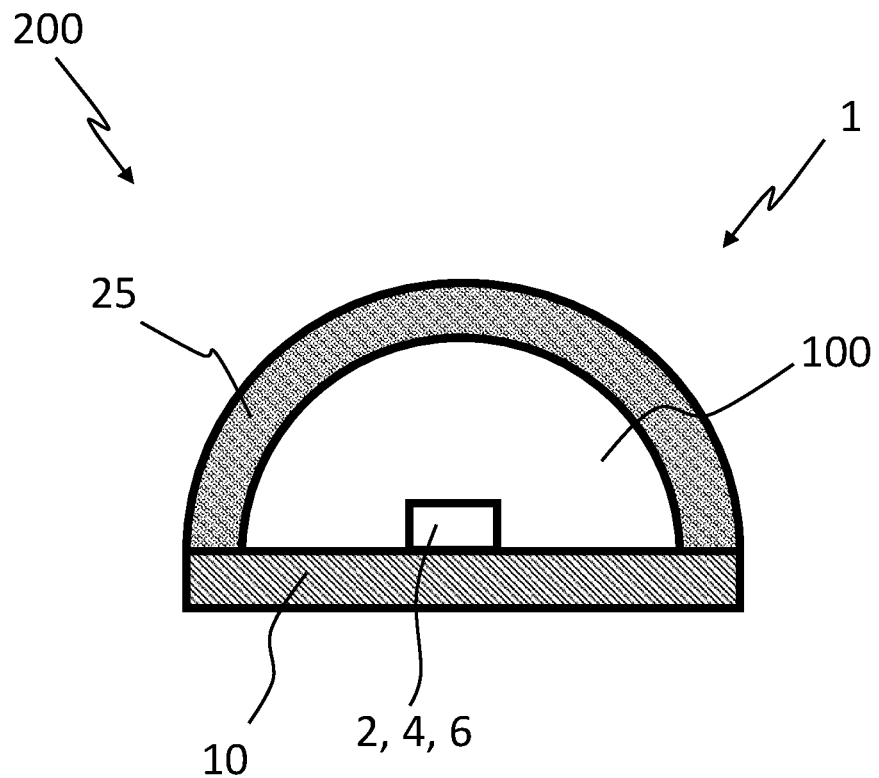
FIGS. 9 and 10 show further embodiments of a measurement device according to the present invention.

FIG. 9 shows an alternative embodiment, in which the chamber walls are formed by the air and water impermeable chamber wall 10 and from a first air and water vapour permeable chamber wall 25. The first air and water vapour permeable chamber wall 25 forms the flow channel and also the first barrier element of the closed air-filled chamber 200. The first air and water vapour permeable chamber wall 25 is made of air and water vapour permeable material. The air and water impermeable chamber wall 10 is made of air and water impermeable material.

The air and water impermeable chamber wall 10 and the air and the first water vapour permeable chamber wall 25 together define the closed air-filled chamber 100 in which the pressure sensor 2 is provided.

Figure 10:
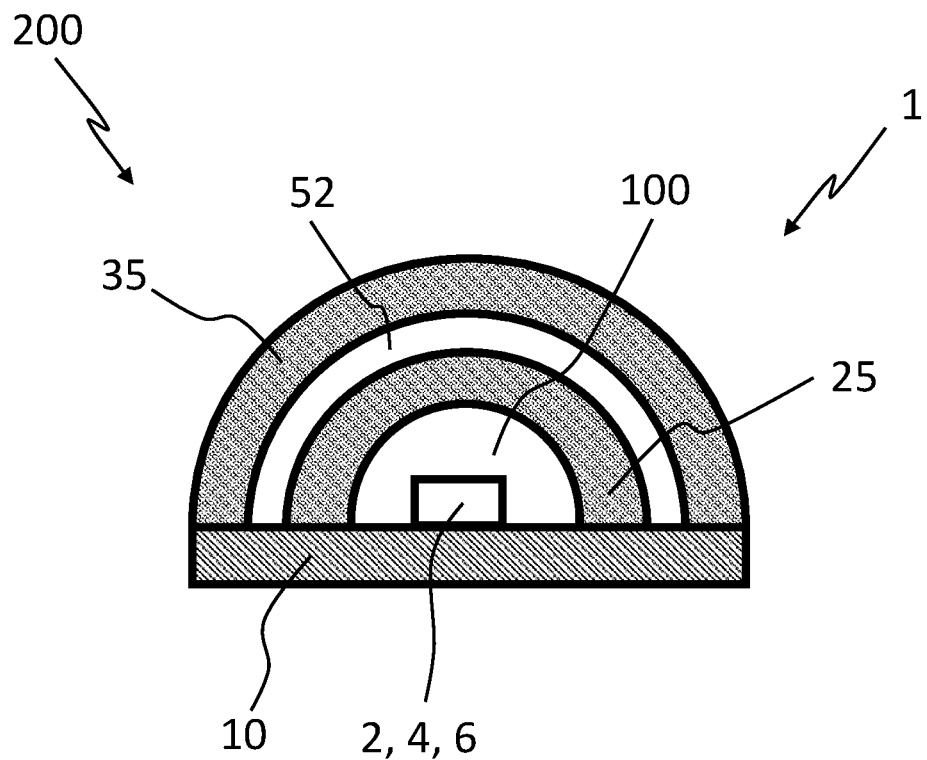

FIG. 10 shows another embodiment, in which the chamber walls are formed by the air and water impermeable chamber wall 10 and from a first air and water vapour permeable chamber wall 25 and a second first air and water vapour permeable chamber wall 35. The first and second air and water vapour permeable chamber walls 25, 35 are arranged at distance from each other such that a second air gap 52 is provided between the first and second air and water vapour permeable chamber walls 25, 35. The second air and water vapour permeable chamber walls 35 are arranged outside the closed air-filled chamber 100. The first and second air and water vapour permeable chamber walls 25, 35 form the flow channel between the closed air-filled chamber 100 and outside of the closed air-filled chamber 200. The first and second air and water vapour permeable chamber wall 25, 35 are made of air and water vapour permeable material. The air and water impermeable chamber wall 10 is made of air and water impermeable material. The second air gap 52 provides a capillary break between the first and second air and water vapour permeable chamber wall 25, 35.

The air and water impermeable chamber wall 10 and the air and the first water vapour permeable chamber wall 25 together define the closed air-filled chamber 100 in which the pressure sensor 2 is provided.

The air and water impermeable chamber wall 10 and the air and the second water vapour permeable chamber wall 35 may together define outer walls of the closed air-filled chamber 200.

In the embodiments of FIGS. 1 to 10, the first barrier element 20, 25 or the second barrier element 30, 35 or the first and second barrier elements 20, 25, 30, 35 are made of porous material for providing air and water vapour permeability.

The porous material of the first and second barrier elements 20, 25, 30, 35 may comprise mineral-based material, concrete, cement-based material, or calcium sulfate dehydrate -based material or mixture thereof.

Pore-size of the porous material of the first and second barrier elements 20, 25, 30, 35 is between 1 to 100 nm, preferably between 3 to 30 nm, and more preferably between 5 to 20 nm.

In some embodiments, pore-size of the porous material of the first and second barrier elements 20, 25, 30, 35 is less than 1 micrometer.

The air and water impermeable material of the chamber walls 10 may be polymer material, metal or the like preventing air and water vapour flow through the chamber walls 10.

The air and water permeable material of the chamber walls 10 or the housing barrier element 41 is porous material for providing air and water vapour permeability. The porous material may comprise mineral-based material, concrete, cement-based material, or calcium sulfate dehydrate -based material or mixture thereof.

Figure 11:
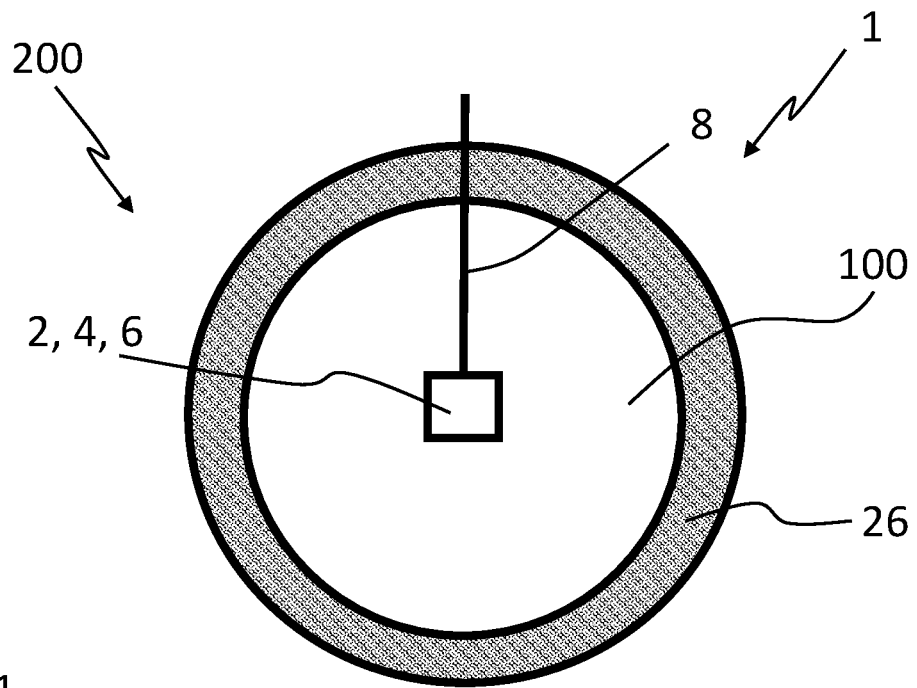
FIGS. 11, 12, 13, 14 and 15 show yet further embodiments of a measurement device according to the present invention.

FIG. 11 shows an embodiment, in which the the chamber walls 26 of the closed air-filled chamber 200 are made air and water vapour permeable material and arranged to define the closed air-filled chamber space 100 inside the closed air-filled chamber 200. Thus, the chamber walls 26 form the flow pat or flow channel and also the barrier element.

The pressure sensor 2, and possible temperature and humidity sensors 4, 6, are supported inside the closed air-filled chamber space 100 with a support member 8 and arranged spaced apart from the chamber walls 26.

In alternative embodiments, the closed air-filled chamber 200 comprises inner chamber walls 26 defining the closed air-filled chamber space 100 inside the closed air-filled chamber 200. The closed air-filled chamber 200 further comprises outer chamber walls 36 arranged to surround the first chamber walls 20 outside the closed air-filled chamber space 100. A closed chamber air gap 53 provided between the inner chamber walls 26 and the outer chamber walls 36 such that the outer chamber walls 36 are provided at a distance from the inner chamber walls 26. The chamber air gap 53 form a capillary break between the inner and outer chamber walls 26, 36.

Figure 12:
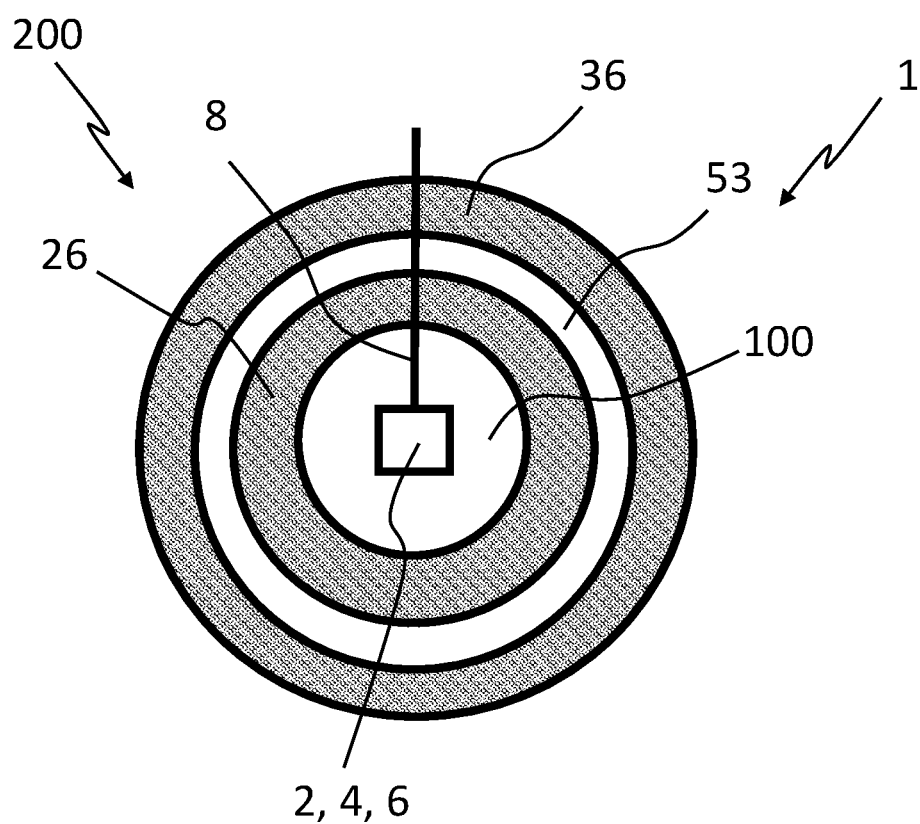

FIG. 12 shows an embodiment, in which the inner chamber walls 26 and the outer chamber walls 36 are made of air and water permeable material allowing air and water vapour flow into the closed air-filled chamber space 100 and out of closed air-filled chamber space 100 through the inner chamber walls 26 and the outer chamber walls 36.

The pressure sensor 2 and possible temperature and humidity sensors 4, 6, are arranged spaced apart from the inner chamber walls 26 and supported with the support member 8.

Figure 13:
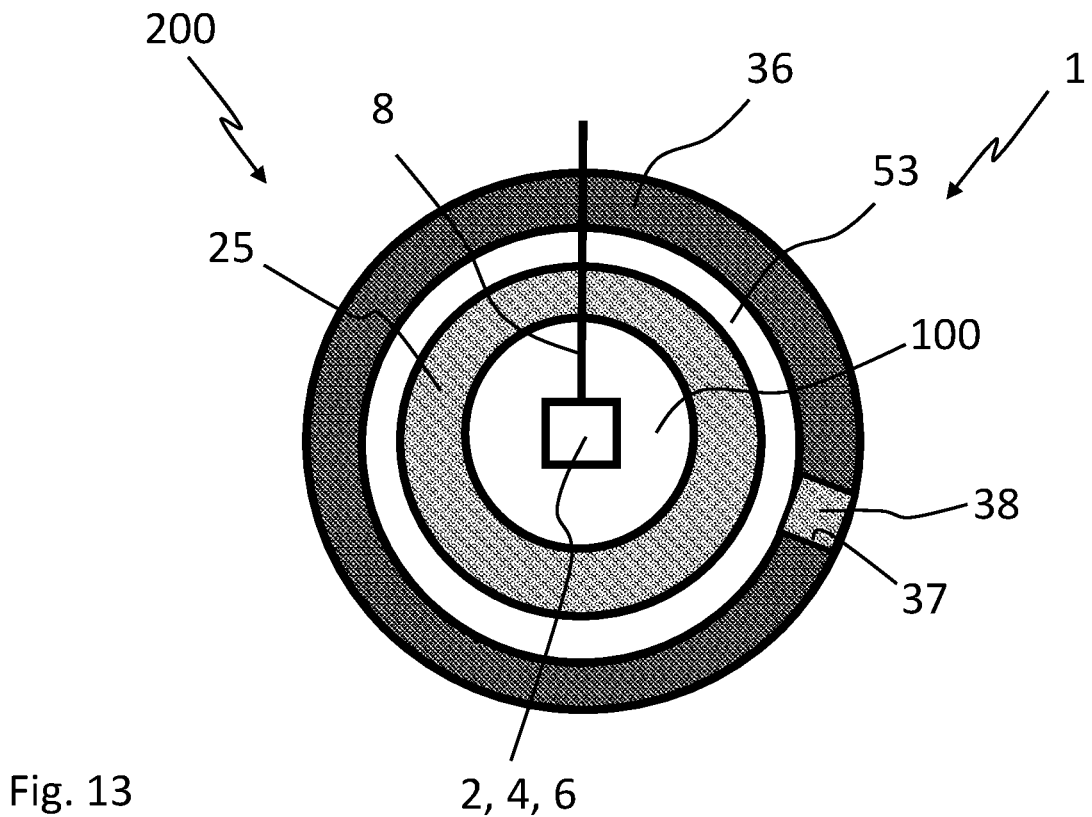

FIG. 13 shows another embodiment, in which the inner chamber walls 26 are made of air and water vapour permeable material and the outer chamber walls 36 are provided air and water vapour impermeable. The outer chamber walls 36 comprise an outer wall flow channel 37 provided with an air and water vapour permeable outer wall barrier element 38 for providing flow path for air and water vapour into the closed air-filled chamber space 100 and out of closed air-filled chamber space 100 through the inner chamber walls 26 and outer wall barrier element 38. The outer wall barrier element 38 is arranged to block or close the outer wall flow channel 37.

Figure 14:
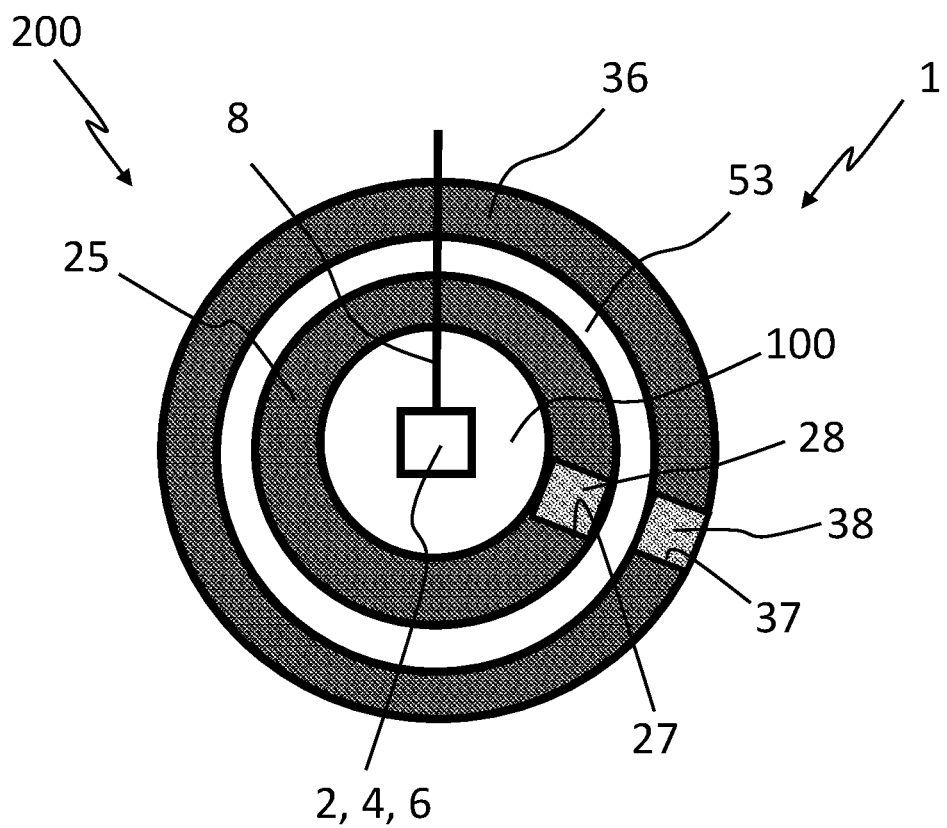

FIG. 14 shows a further embodiment, in which the inner chamber walls 26 are provided air and water vapour impermeable and comprise an inner wall flow channel 27 provided with an air and water vapour permeable inner wall barrier element 28. The outer chamber walls 32 are provided air and water vapour impermeable and comprise an outer wall flow channel 37 provided with an air and water vapour permeable outer wall barrier element 38. Accordingly, a flow path for air and water vapour flow into the closed air-filled chamber space 100 and out of closed air-filled chamber space 100 is provided through the inner wall barrier element 28 and outer wall barrier element 38. The inner wall barrier element 28 is arranged to block or close the inner wall flow channel 27. The outer wall barrier element 38 is arranged to block or close the outer wall flow channel 37.

Figure 15:
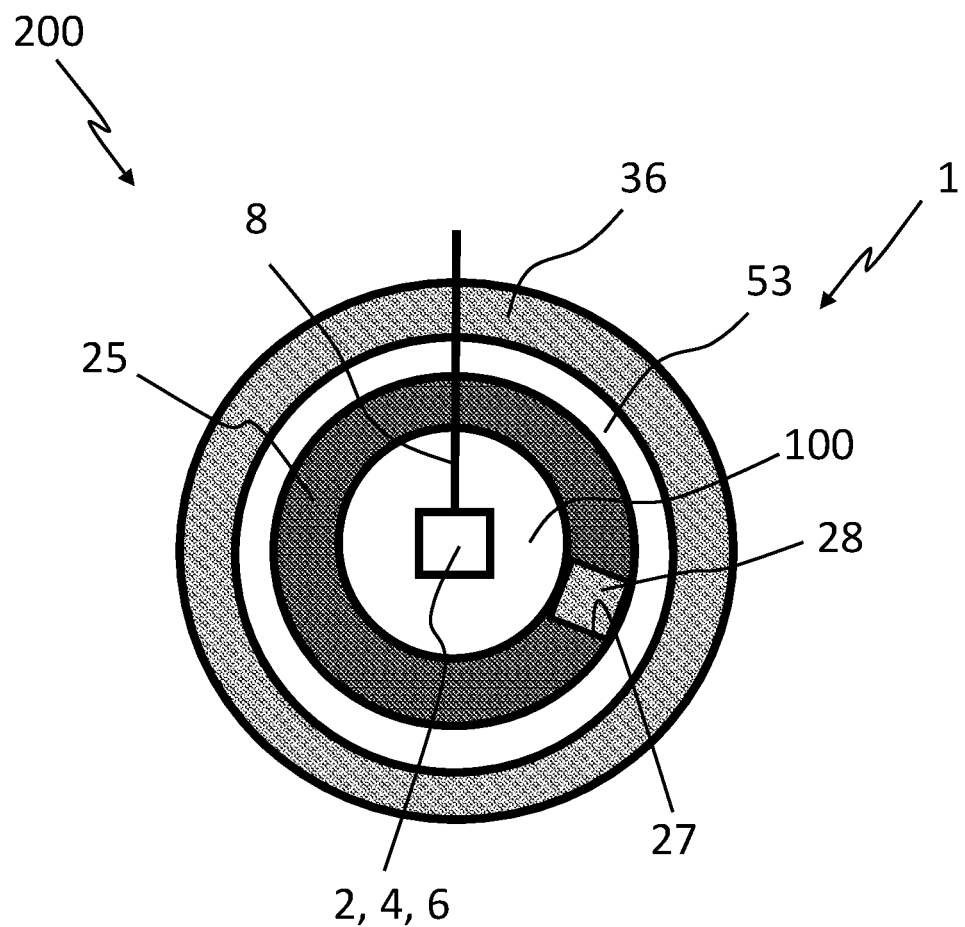

FIG. 15 shows yet a further embodiment, in which the inner chamber walls 26 are provided air and water vapour impermeable and comprise an inner wall flow channel 27 provided with an air and water vapour permeable inner wall barrier element 28. The outer chamber walls 36 are made of air and water vapour permeable material. Accordingly, a flow path for air and water vapour flow into the closed air-filled chamber space 100 and out of closed air-filled chamber space 100 is provided through the inner wall barrier element 28 and the outer chamber walls 36. The inner wall barrier element 28 is arranged to block or close the inner wall flow channel 27.

In the embodiments of FIGS. 11 to 15 the air and water vapour permeable material of the inner chamber walls 26 and the outer chamber walls 36 is porous material for providing air and water vapour permeability.

The air and water vapour permeable porous material of the inner chamber walls 26 and the outer chamber walls 36 may comprise mineral-based material, concrete, cement-based material or calcium sulfate dehydrate-based material or mixture thereof.

Similarly, the inner wall barrier element 28 and the outer wall barrier element 38 are made of porous material for providing air and water vapour permeability.

The porous material of the inner wall barrier element 28 and the outer wall barrier element 38 may comprise mineral-based material, concrete, cement-based material, or calcium sulfate dehydrate -based material or mixture thereof.

Pore-size of the porous material of the inner wall barrier element 28 and the outer wall barrier element 38, or the inner chamber walls 26 and the outer chamber walls 36 is between 1 to 100 nm, preferably between 3 to 30 nm, and more preferably between 5 to 20 nm.

In some embodiments, pore-size of the porous material of the inner wall barrier element 28 and the outer wall barrier element 38, or the inner chamber walls 26 and the outer chamber walls 36 is less than 1 micrometre.

The air and water impermeable material of the air and water vapour impermeable inner chamber walls 26 and the outer chamber walls 36 may be polymer material, metal or the like preventing air and water vapour flow through the inner chamber walls 26 and the outer chamber walls 36.

The invention has been described above with reference to the examples shown in the figures. However, the invention is in no way restricted to the above examples but may vary within the scope of the claims.

The invention claimed is:

1. A measurement device for measuring concrete curing, wherein the measurement device comprises:
   an air-filled chamber;
   chamber walls defining an air-filled chamber space inside the air-filled chamber; and
   a pressure sensor provided inside the air-filled chamber space of the air-filled chamber,
   wherein the chamber walls comprise a flow channel between the air-filled chamber space inside the air-filled chamber and the outside the air-filled chamber,
   wherein the flow channel comprises a first barrier element arranged to define the air-filled chamber space together with the chamber walls, the first barrier element being air and water vapour permeable, and
   wherein the flow channel comprises a second barrier element arranged to the flow channel outside the air-filled chamber space and at distance from the first barrier element such that a first air gap is provided between the first and second barrier elements, the second barrier element being air and water vapour permeable for providing a flow path for air and water vapour to flow into the air-filled chamber space and out of the air-filled chamber space.

2. The measurement device according to claim 1, wherein the chamber walls are made of air and water vapour permeable material and arranged to define the air-filled chamber space inside the air-filled chamber.

3. The measurement device according to claim 2, wherein the air-filled chamber comprises:
   inner chamber walls defining the air-filled chamber space inside the air-filled chamber, and outer chamber walls arranged to surround the inner chamber walls outside the air-filled chamber space, wherein at least one of:
   the air and water vapour permeable material of the inner chamber walls and the outer chamber walls is porous material for providing air and water vapour permeability; or
   the air and water vapour permeable material of the inner chamber walls and the outer chamber walls is porous material and comprises at least one of the following:
   mineral-based material; or
   concrete; or
   cement-based material; or
   calcium sulfate dehydrate-based material.

4. The measurement device according to claim 1, wherein the air-filled chamber comprises:
   inner chamber walls defining the air-filled chamber space inside the air-filled chamber;
   outer chamber walls arranged to surround the inner chamber walls outside the air-filled chamber space; and
   a chamber air gap provided between the inner chamber walls and the outer chamber walls such that the outer chamber walls are provided at a distance from the inner chamber walls.

5. The measurement device according to claim 4, wherein at least one of:
   the inner chamber walls and the outer chamber walls are made of air and water vapour permeable material allowing air and water vapour flow into the air-filled chamber space and out of the air-filled chamber space through the inner chamber walls and the outer chamber walls; or
   the inner chamber walls are made of air and water vapour permeable material and the outer chamber walls are provided air and water vapour impermeable and comprise an outer wall flow channel provided with an air and water vapour permeable outer wall barrier element for providing flow path for air and water vapour into the air-filled chamber space and out of the air-filled chamber space through the inner chamber walls and outer wall barrier element; or
   the inner chamber walls are provided air and water vapour impermeable and comprise an inner wall flow channel provided with an air and water vapour permeable inner wall barrier element and the outer chamber walls are provided air and water vapour impermeable and comprise an outer wall flow channel provided with an air and water vapour permeable outer wall barrier element for providing flow path for air and water vapour flow into the air-filled chamber space and out of the air-filled chamber space through the inner wall barrier element and outer wall barrier element; or
   the inner chamber walls are provided air and water vapour impermeable and comprise an inner wall flow channel provided with an air and water vapour permeable inner wall barrier element and the outer chamber walls are made of air and water vapour permeable material for providing flow path for air and water vapour flow into the air-filled chamber space and out of the air-filled chamber space through the inner wall barrier element and the outer chamber walls.

6. The measurement device according to claim 5, wherein at least one of:
   the inner wall barrier element and the outer wall barrier element are made of porous material for providing air and water vapour permeability; or
   the inner wall barrier element and the outer wall barrier element are made of porous material for providing air and water vapour permeability, the porous material of the inner wall barrier element and the outer wall barrier element comprising one of the following:
   mineral-based material; or
   concrete; or
   cement-based material; or
   calcium sulfate dehydrate-based material.

7. The measurement device according to claim 6, wherein the pore-size of the porous material of the inner wall barrier element and the outer wall barrier element is between at least one of:
   1 to 100 nm; or
   3 to 30 nm; or
   5 to 20 nm.

8. The measurement device according to claim 1, wherein at least one of:
   at least one of the first barrier element or the second barrier element is made of porous material for providing air and water vapour permeability; or
   at least one of the first barrier element or the second barrier element is made of porous material for providing air and water vapour permeability, the porous material of the first and second barrier elements comprising one of the following:
mineral-based material; or
concrete; or
cement-based material; or
calcium sulfate dehydrate-based material.

9. The measurement device according to claim 8, wherein the pore-size of the porous material of the first and second barrier elements is between at least one of:
1 to 100 nm; or
3 to 30 nm; or
5 to 20 nm.

10. The measurement device according to claim 1, wherein at least one of:
the measurement device comprises a housing surrounding the air-filled chamber, the housing being air and water vapour permeable; or
the measurement device comprises a housing surrounding the air-filled chamber, the housing comprising a housing barrier element, the housing barrier element being air and water vapour permeable and arranged to provide flow path for air and water vapour between the air-filled chamber and outside of the housing.

11. The measurement device according to claim 10, wherein the air and water vapour permeable housing or the air or water vapour permeable housing barrier element is arranged to form the first barrier element or the second barrier element.

12. The measurement device according to claim 1, wherein the measurement device comprises a housing surrounding the air-filled chamber, the housing comprising one or more openings, arranged to provide flow path for air and water vapour between the air-filled chamber and outside of the housing.

13. The measurement device according to claim 1, wherein the air-filled chamber space further comprises at least one of a temperature sensor or a humidity sensor, or a temperature sensor and a humidity sensor.

14. The measurement device according to claim 1, wherein the chamber walls are permeable to air and water vapour to allow air and water vapour to flow into the air-filled chamber space and out of the air-filled chamber space.

15. The measurement device according to claim 1, wherein the chamber walls are impermeable to air and water vapour.

16. A measurement device for measuring concrete curing, wherein the measurement device comprises:
an air-filled chamber;
chamber walls defining an air-filled chamber space inside the air-filled chamber; and
a pressure sensor provided inside the air-filled chamber space of the air-filled chamber,
wherein the chamber walls are made of air and water vapour permeable material and are arranged to define the air-filled chamber space inside of the air-filled chamber, and
wherein the air-filled chamber includes inner chamber walls defining the air-filled chamber space inside the air-filled chamber, outer chamber walls arranged to surround the inner chamber walls outside the air-filled chamber space, and a chamber air gap provided between the inner chamber walls and the outer chamber walls such that the outer chamber walls are provided at a distance from the inner chamber walls.

* * * * *